United States Patent [19]
Ryden

[11] Patent Number: 6,049,917
[45] Date of Patent: *Apr. 18, 2000

[54] AIR INJECTION SPORTS GOGGLE AND METHOD

[75] Inventor: William Dennis Ryden, Colorado Springs, Colo.

[73] Assignee: Smith Sport Optics

[ * ] Notice: This patent is subject to a terminal disclaimer.

[21] Appl. No.: 09/012,951

[22] Filed: Jan. 23, 1998

[51] Int. Cl.⁷ .................................................. A61F 9/02
[52] U.S. Cl. .................................. 2/436; 2/171.3
[58] Field of Search ........................ 2/8, 9, 171.3, 436, 2/437

[56] References Cited

U.S. PATENT DOCUMENTS

| | | |
|---|---|---|
| 3,377,626 | 4/1968 | Smith . |
| 3,691,565 | 9/1972 | Galonek ................................... 2/14 H |
| 3,825,953 | 7/1974 | Hunter ..................................... 2/14 K |
| 4,150,443 | 4/1979 | McNeilly .................................... 2/436 |
| 4,309,774 | 1/1982 | Guzowski ....................................... 2/8 |
| 4,443,893 | 4/1984 | Yamamoto .................................. 2/436 |
| 5,031,237 | 7/1991 | Honrud .......................................... 2/8 |
| 5,123,114 | 6/1992 | Desanti ........................................... 2/8 |
| 5,452,480 | 9/1995 | Ryden ........................................ 2/436 |
| 5,542,130 | 8/1996 | Grabos, Jr. et al. ......................... 2/436 |
| 5,996,746 | 10/1999 | Reedy et al. ................................ 2/436 |

OTHER PUBLICATIONS

Loren Mooney, In the Clear, Sports Illustrated, vol. 89, p. 41, Dec. 28, 1998.

*Primary Examiner*—John J. Calvert
*Assistant Examiner*—Katherine Moran
*Attorney, Agent, or Firm*—Dale B. Halling

[57] ABSTRACT

An air injection sports goggle (10) has a lens subframe (14) connected to a face flange subframe (16) by struts (18). The struts (18) form a top opening (20) and a pair of cheek openings (22) between the lens subframe (14) and the face flange subframe (16). A lens (24) is contained in the lens subframe (14). A cover fits (46) over the top opening (20). A pair of open cell foam vents (52) are located in the pair of cheek openings (22). An air injection hole (54) provides access between an outside and an interior space. A ventilating fan (12) located in the top opening (20) pulls air in through the air injection hole (54) and the pair of cheek openings (22) and exhausts the air through the top opening (20).

18 Claims, 3 Drawing Sheets

AIR INJECTION SPORTS GOGGLE AND METHOD

FIELD OF THE INVENTION

The present invention relates generally to the field of sports goggles and more particularly to an air injection sports goggle and method.

BACKGROUND OF THE INVENTION

Sports goggles have been used to protect the user from foreign objects, sun and wind. One problem that has occurred with sports goggles is that they have a tendency to fog. This problem is particularly troublesome for users that wear corrective glasses. In this case the corrective lenses have an even greater tendency to fog. Many types of sports goggles attempt to avoid this by having air vents that allow cooler, drier air to circulate through the enclosed space of the goggle. The cooler, drier air lowers the dew point of the air inside the goggle and eliminates the fog. Unfortunately, the air vents help most while the user is moving and provide very little relief once the user has stopped moving. In addition, while the user is moving the goggle lens and corrective lenses' temperature are lowered. Because the goggle lens and corrective lenses' temperature are lowered while the user is moving, both types of lenses are more likely to fog over when the user stops moving.

Some manufacturers of sports goggles have added circulating or ventilating fans in the top of their sports goggles. Unfortunately, these fans are unable to significantly replace (remove) the moist air (high dew point) between the user's eye socket and the user's corrective lens. As a result, these fans provide very little relief from fog on the user's corrective lenses.

Thus there exists a need for a sports goggle with a ventilating fan that can reduce or eliminate the fogging of a user's corrective lenses.

DETAILED DESCRIPTION OF THE DRAWINGS

The air injection sports goggle of the invention has a lens subframe having a lens contained therein. A face flange subframe is connected to the lens subframe by struts. The struts form a top opening and a pair of cheek openings between the lens subframe and the face flange subframe. A cover and a ventilating fan are placed over the top opening. A pair of open cell foam vents are placed over the pair of cheek openings. An air injection hole is provided between the outside and an interior space. The ventilating fan pulls air in through the air injection hole and the pair of cheek openings and exhausts the air through the top opening. The air injection sports goggle described herein causes dry air (low dew point air) to be injected from the air injection hole into the space between a user's eye socket and the user's corrective lenses. As a result the dew point in the space between the eye socket and the corrective lenses is significantly lowered and fogging of the corrective lenses is reduced or eliminated.

Figure 1:
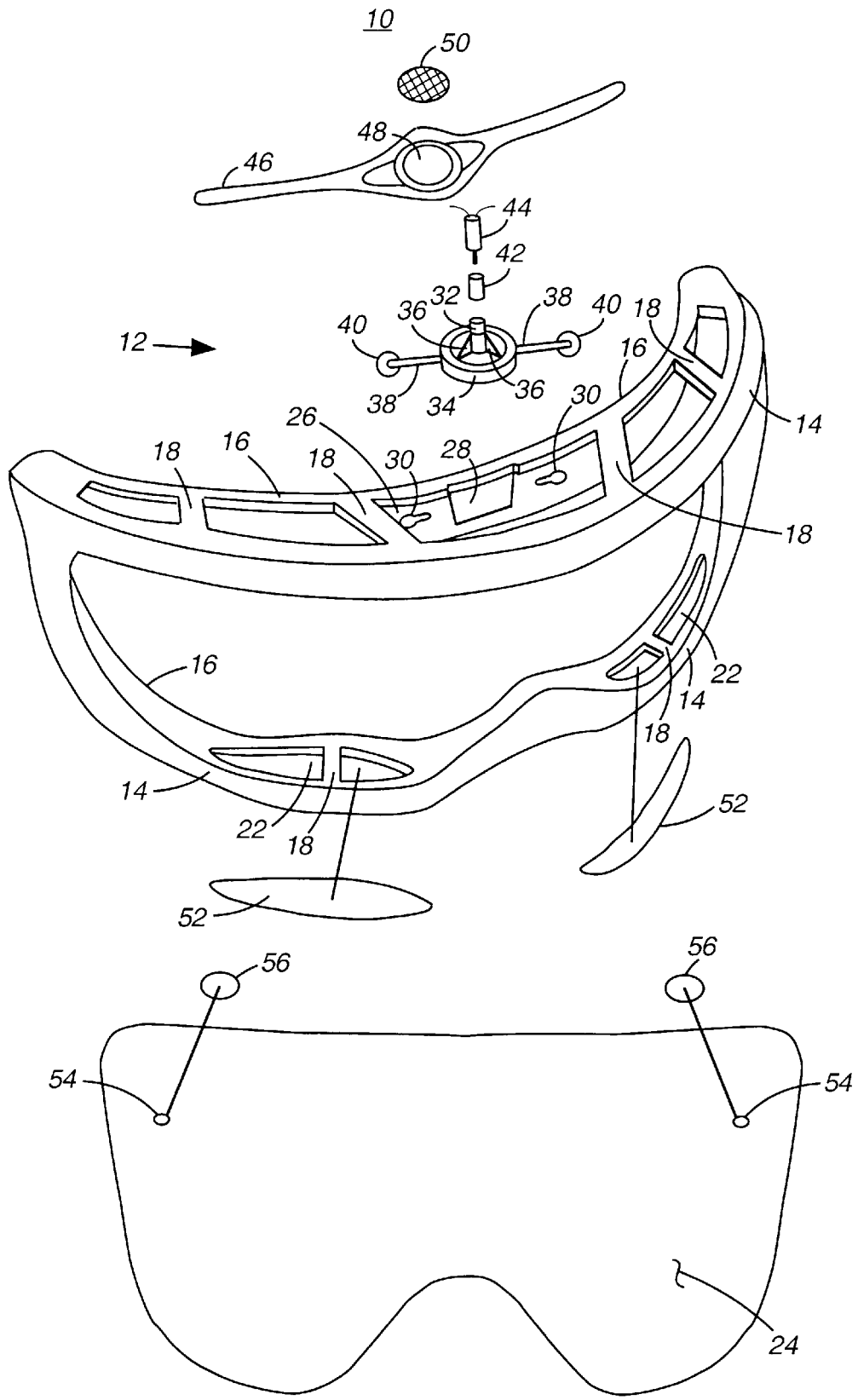
FIG. 1 is an exploded view of an air injection sports goggle in accordance with one embodiment of the invention.

FIG. 1 is an exploded view of an air injection sports goggle in accordance with one embodiment of the invention. The sports goggle 10 includes a lens subframe 14 connected to a face subframe 16 by a plurality of spacer struts 18. The spacer struts 18 form a top open portion (top brim) 20 and a pair of cheek open portions 22. A lens 24 fits in the lens subframe 14. The face subframe 16 has a face flange 26 that conforms to a user's face. The face flange 26 has a trapezoidal opening 28 in a forehead portion of the face flange 26. A pair of locking holes 30 are located on either side of the trapezoidal opening 28.

A ventilating fan assembly 12 fits inside the top opening 20. The ventilating fan assembly has a motor mount boss 32 connected to a fan shroud 34 by a race strut 36. A pair of flexible face flange struts (pair of flexible face flange mounting struts) 38 are attached to the fan shroud 34. A plurality of fan blades rotate freely inside the fan shroud 34. At the free end of the pair of flexible face flange mounting struts 38 are a pair of dumbbell flanges (pair of mating buttons) 40. The dumbbell flanges 40 are inserted into the locking holes (pair of keyholes) 30, to hold the fan assembly 12 against the face flange 26 between the lens subframe 14 and the face subframe 16. The fan shroud 34 extends into the trapezoidal opening 28. A foam face buffer covers the face flange and prevents the user from feeling the mating buttons 40 or the fan shroud 34. A foam sleeve 42 fits over an electric motor 44. The foam sleeve 42 isolates the vibration of the motor 44 from the motor mount boss 32. This reduces the noise from the motor 44. The motor 44 with the foam sleeve fits inside the motor mount boss 32. In one embodiment the motor is a coreless fan motor. The coreless fan motor can be an electronic commutator motor having three windings.

A cover 46 having an opening 48 for the fan exhaust vent fits over the top open portion 20. In one embodiment the cover (air impermeable cover) 46 is made of an air impermeable material such as a closed cell foam. An air permeable foam (fan exhaust vent foam) 50 fits over the exhaust vent 48 of the high pressure side of the fan. The sports goggle 10 generally includes a head strap attached to the ends of the frame.

A pair of air permeable foam vents (pair of open cell foam vents, pair of cheek opening baffles) 52 fit in the pair of cheek openings 22. The lens (protective lens) 24 of the sports goggle has an air injection hole 54. In one embodiment multiple air injection holes 54 are placed on either/both the left and right sides of the sports goggle. In another embodiment the air injection hole 54 is located in the lens subframe 14 and provides access between the outside and the inside of the sports goggle. The air injection hole 54 is positioned near a line that runs tangential to a user's eye balls and the style of the goggles then determines whether the air injection hole 54 is in the lens 24 or the lens subframe 14. In one embodiment the air injection hole 54 is used only on the weak side of the ventilating fan. The weak side is the left eye socket if the blade exhausts air with counter clockwise rotation (view from above the goggle) and is the right eye socket if this blade rotation is clockwise. An open cell foam cover 56 is located over the air injection hole 54.

The open cell foam cover 56 and cheek vent foam 52 serve two purposes. One purpose of the foam is to prevent snow, dust or debris from entering the sports goggles. The other is to direct the air flow from the air injection hole 54. By properly calibrating the sports goggle the air flow from the air injection hole 54 is directed between the user's eye socket and a corrective lens. The air flow between the user's eye socket and the corrective lens is an eye socket air flow. The corrective lens can be either a standard eyeglasses corrective lens or a specially designed corrective lens designed to fit within the sports goggle 10. Other factors that must be considered are that too high of an eye socket air flow can result in irritation and drying of the user's eyes and too low of an air flow will not defog the corrective lens. Present experience has placed the optimal eye socket air flow between 0.025 and 0.051 meters per second.

The fan 12 is designed to pull air in from the cheek openings 22 and the air injection hole 54 and exhaust the air out the exhaust vent 50 at the top of the goggles. Since the top cover 46 is air impermeable, the fan 12 exhausts air faster when a user is not moving. As the user moves the air pressure on the top of the sports goggle increases and this reduces the air flow the fan can support. This has the beneficial effect of not overly cooling the user's corrective lenses as the user moves.

Figure 2:
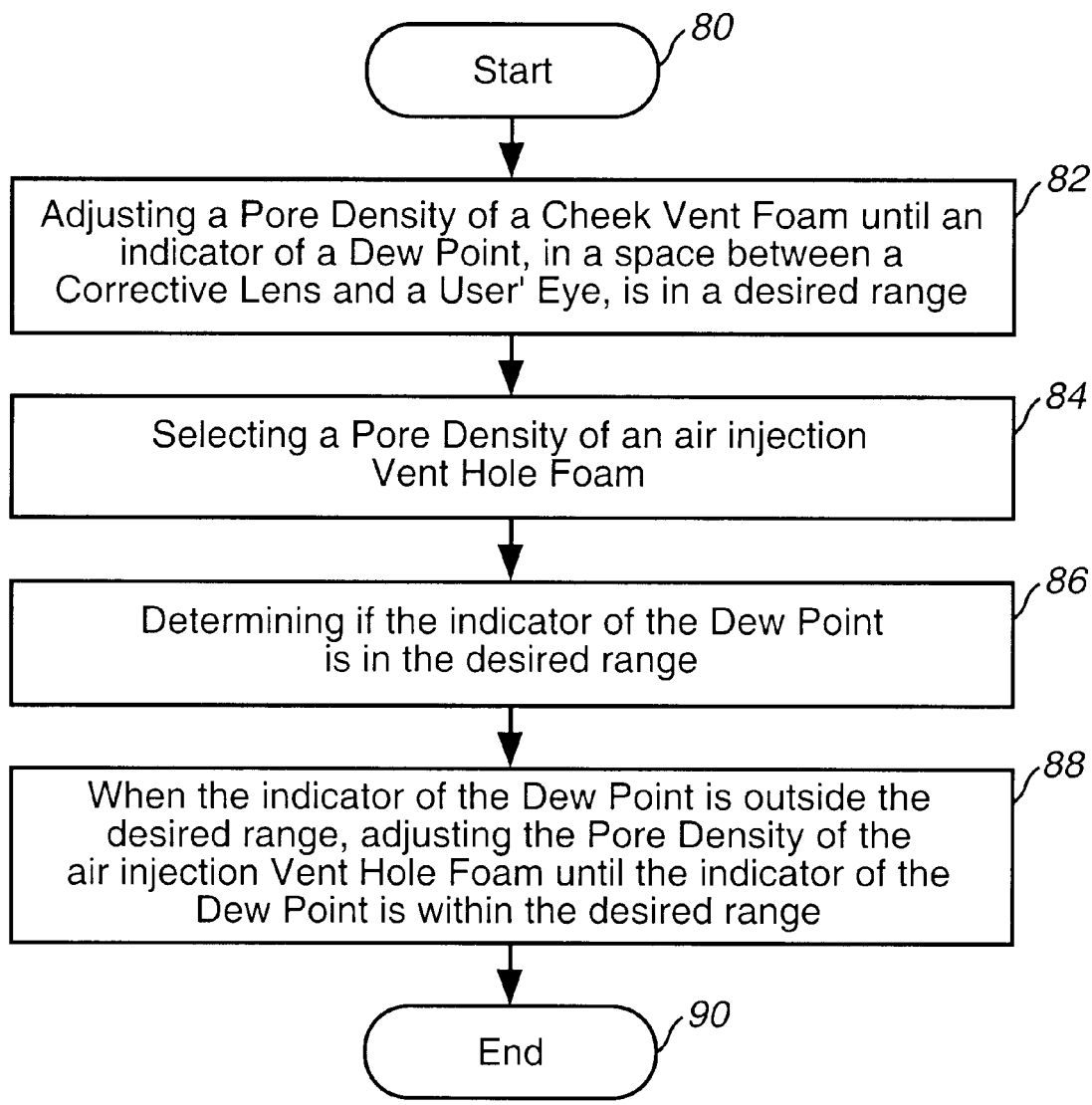
FIG. 2 is a flow chart of a process for calibrating an air injection sports goggle in accordance with one embodiment of the invention.

FIG. 2 is a flow chart of a process for calibrating an air injection sports goggle in accordance with one embodiment of the invention. The process starts, step 80, by adjusting the pore density of a cheek vent foam until an indicator of a dew point inside the air injection sports goggle is in a desired range at step 82. As a general rule the higher the pore density of the foam the less air the foam allows to flow through it. Alternatively, the area of the vents can be adjusted to change the air flow. The indicator of the dew point can be measured using a hygrometer to directly determine the dew point or a hot wire anemometer can be used to determine the air flow. Next, the pore density of the air injection vent hole foam is selected at step 84. Then it is determined if the indicator of the dew point is in the desired range at step 86. At step 88, adjusting the pore density of the air injection vent hole foam until the indicator of the dew point is within the desired range, when the indicator of the dew point is outside the desired range which ends the processes at step 90.

The process of FIG. 2 can be understood in terms of the discussion given here. Increasing the pore density of the cheek vent foam causes the pressure differential of air between the inside and the outside of the goggle to increase, thereby increasing the air flow through the injection hole. If the pressure differential is too high, air flow through the injection hole may be too high to be comfortable, while if the pressure differential is too low the air flow through injection hole may be insufficient for effective defogging. Part of the air flow through the injection vent flows in front of the eyeglass lens and part of it flows between the eye socket and the eyeglass lens (eye socket air flow). As the pore density of the open cell foam cover is increased from a low value, both the total amount of air flow through the injection hole and the fraction of that air flow that is eye socket air flow will decrease. Thus even under conditions where a high pressure differential exists and there is high air flow through the injection hole, eye socket air flow may be too low because the pore density of the open cell foam cover is not optimum. The process or FIG. 2 allows the selection of this optimum pore density for both the cheek vent foam and the open cell foam cover.

Figure 3:
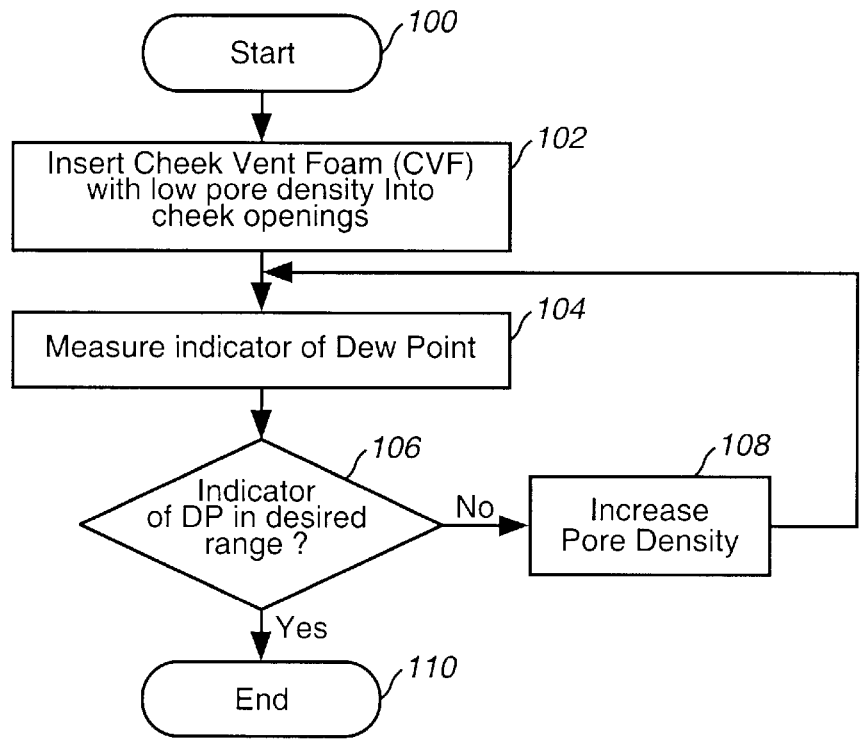
FIG. 3 is a flow chart of part of a process for calibrating an air injection sports goggle in accordance with one embodiment of the invention.

FIG. 3 is a flow chart of part of a process for calibrating an air injection sports goggle in accordance with one embodiment of the invention. This flow chart is a more detailed process for performing step 82 of the flow chart of FIG. 2. The process starts, step 100, by inserting a cheek vent foam having a low pore density into the cheek openings at step 102. Note that this process is ideally performed without any foam over the air injection vent hole. The indicator of the dew point is then measured between a user's eye socket and the corrective lens at step 104. Next, it is determined if the indicator of the dew point (DP) is in the desired range at step 106. When the indicator of the dew point is not in the desired range, the pore density of the cheek vent foam is increased at step 108 and processing then returns to step 104. When the indicator of the dew point is in the desired range, the process ends at step 110.

Figure 4:
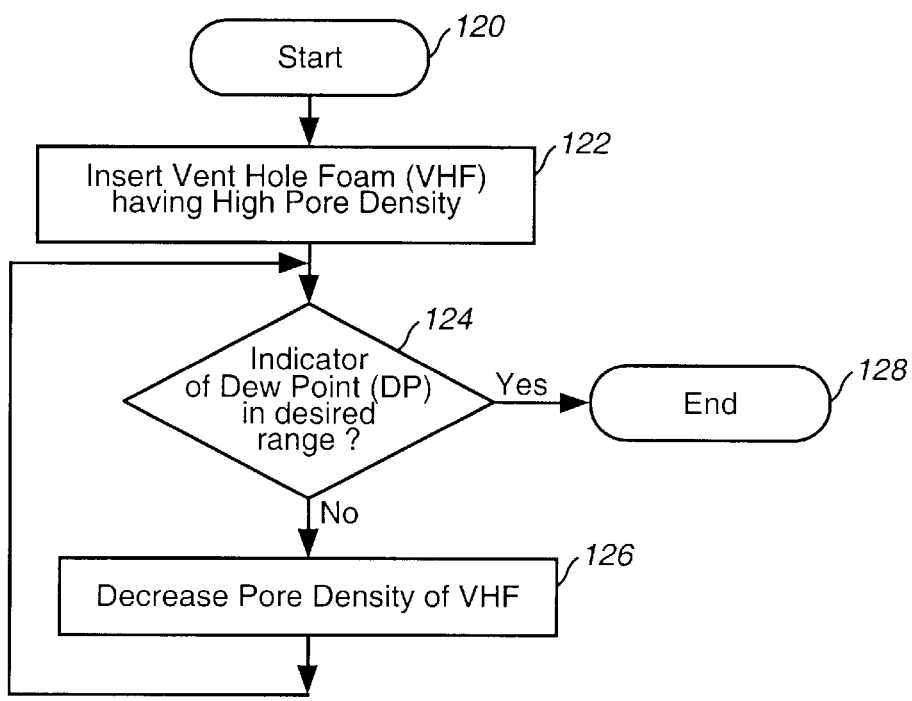
FIG. 4 is a flow chart of part of a process for calibrating an air injection sports goggle in accordance with one embodiment of the invention.

FIG. 4 is a flow chart of part of a process for calibrating an air injection sports goggle in accordance with one embodiment of the invention. The process of FIG. 4 describes in more detail one way of adjusting the vent hole foam pore density. The process starts, step 120, by inserting a vent hole foam having a high pore density at step 122. Next, it is determined if the indicator of the dew point is in the desired range at step 124. When the indicator of the dew point is not in the desired range, decreasing the pore density of the vent hole foam at step 126 and returning to step 124. When the indicator of the dew point is in desired range, ending the process at step 128.

Thus there has been described an air injection sports goggle that can significantly reduce or eliminate the fogging of a user's corrective lenses.

While the invention has been described in conjunction with specific embodiments thereof, it is evident that many alterations, modifications, and variations will be apparent to those skilled in the art in light of the foregoing description. Accordingly, it is intended to embrace all such alterations, modifications, and variations in the appended claims.

What is claimed is:

1. An air injection sports goggle comprising:
   a lens subframe;
   a lens contained in the lens subframe
   a face flange subframe connected to the lens subframe by a plurality of struts, the plurality of struts forming a top opening and a pair of cheek openings between the lens subframe and the face flange subframe;
   a cover over the top opening;
   a pair of open cell foam vents located in the pair of cheek openings;
   an air injection hole providing access between an outside and an interior space between the lens subframe and a user; and
   a ventilating fan located in the top opening for pulling air in through the air injection hole and the pair of cheek openings and exhausting the air through the top opening.

2. The air injection sports goggle of claim 1, wherein the top opening has an exhaust vent.

3. The air injection sports goggle of claim 2, wherein the cover is made of a closed cell foam.

4. The air injection sports goggle of claim 1, wherein the air injection hole is located near a line tangential to a user's eye balls.

5. The air injection sports goggle of claim 4, wherein the air injection hole is located in the lens.

6. The air injection sports goggle of claim 4, wherein the air injection hole is located in the lens subframe.

7. The air injection sports goggle of claim 1, wherein the air injection hole is located on a weak side of the ventilating fan.

8. The air injection sports goggle of claim 1, further including an open cell foam cover located over the air injection hole.

9. A method of calibrating an air injection sports goggle, comprising the steps of:
- (a) adjusting a pore density of a cheek vent foam until an indicator of a air flow, in a space between a corrective lens and a user' eye, is in a desired range;
- (b) selecting a pore density of an air injection vent hole foam;
- (c) determining if the indicator of the air flow is in the desired range; and
- (d) when the indicator of the air flow is outside the desired range, adjusting the pore density of the air injection vent hole foam until the indicator of the air flow is within the desired range.

10. The method of claim 9, wherein step (a) further includes the steps of:
- (a1) inserting a cheek vent foam having a low pore density into a cheek opening;
- (a2) measuring the indicator of the air flow inside the air injection sports goggle;
- (a3) determining if the indicator of the air flow is in the desired range;
- (a4) when the indicator of the air flow is not in the desired range, increasing the pore density of the cheek vent foam and returning to step (a2); and
- (a5) when the indicator of the air flow is in the desired range, selecting the pore density of the cheek vent foam in the air injection sport goggle as a desired porosity.

11. The method of claim 9, wherein step (d) further includes the steps of:
- (d1) decreasing the pore density of the air injection vent hole foam;
- (d2) measuring the indicator of the air flow;
- (d3) when the indicator of the air flow is outside the desired range, returning to step (d1);
- (d4) when the indicator of the air flow is within the desired range, selecting the pore density of the air injection vent foam in the air injection sports goggle as a desired porosity.

12. An air injection sports goggle, comprising:
- a frame having a top opening and a pair of cheek openings;
- a protective lens covering a front part of the frame;
- a fan located in the top opening; and
- an air injection hole providing access between an interior space, between the lens subframe and a user, and an outside.

13. The air injection sports goggle of claim 12, wherein the air injection hole is in the protective lens.

14. The air injection sports goggle of claim 12, wherein the air injection hole is in an exterior portion of the frame.

15. The air injection sports goggle of claim 12, wherein the air injection hole is located near a line running tangentially to an eye balls of a user.

16. The air injection sports goggle of claim 12, wherein the fan is designed to pull air in through the air injection hole.

17. The air injection sports goggle of claim 12, further including an air impermeable cover over the top opening, the air impermeable cover having an exhaust vent.

18. The air injection sports goggle of claim 12, further including a pair of cheek opening baffles.

* * * * *